United States Patent [19]

Krause

[11] Patent Number: 5,672,945

[45] Date of Patent: Sep. 30, 1997

[54] MOTOR CONTROLLED SURGICAL SYSTEM AND METHOD HAVING SELF CLEARING MOTOR CONTROL

[75] Inventor: Kenneth W. Krause, Sandown, N.H.

[73] Assignee: Smith & Nephew Endoscopy, Inc., Andover, Mass.

[21] Appl. No.: 630,523

[22] Filed: Apr. 10, 1996

Related U.S. Application Data

[63] Continuation-in-part of Ser. No. 420,243, Apr. 11, 1995, Pat. No. 5,602,449, which is a continuation-in-part of Ser. No. 135,297, Oct. 12, 1993, abandoned, which is a continuation-in-part of Ser. No. 867,871, Apr. 13, 1992, Pat. No. 5,270,622.

[51] Int. Cl.$^6$ .............................. H02P 1/22; H02H 7/085; A61B 17/32

[52] U.S. Cl. .......................... 318/434; 318/264; 318/282; 128/755

[58] Field of Search ...................................... 318/138, 254, 318/256, 257, 264, 280, 281, 282, 434; 128/751, 755; 604/19, 22; 606/53, 79, 118, 167–171, 174, 180

[56] References Cited

U.S. PATENT DOCUMENTS

| Re. 34,556 | 3/1994 | Sjostrom et al. | 606/170 |
|---|---|---|---|
| 4,200,106 | 4/1980 | Douvas et al. | 128/305 |
| 4,298,074 | 11/1981 | Mattchen . | |
| 4,345,192 | 8/1982 | Kohzai et al. . | |
| 4,403,179 | 9/1983 | Kohzai et al. | 318/632 |
| 4,705,038 | 11/1987 | Sjostrom et al. | 128/305 |
| 4,867,155 | 9/1989 | Isaacson | 128/305 |
| 4,995,877 | 2/1991 | Ams et al. | 606/180 |
| 5,017,846 | 5/1991 | Young et al. . | |
| 5,030,900 | 7/1991 | Kono et al. | 318/592 |
| 5,060,658 | 10/1991 | Dejter, Jr. et al. | 128/753 |
| 5,171,245 | 12/1992 | Cezana | 606/86 |
| 5,207,697 | 5/1993 | Carusillo et al. | 606/167 |
| 5,269,794 | 12/1993 | Rexroth | 606/180 |
| 5,270,622 | 12/1993 | Krause | 318/254 |

FOREIGN PATENT DOCUMENTS

| 27 57 132 | 6/1978 | Germany . |
|---|---|---|
| 61-114304 | 6/1986 | Japan . |
| 1074089 | 3/1989 | Japan . |
| 2 156 172 A | 3/1985 | United Kingdom . |
| WO 95/03001 | 2/1995 | WIPO . |

OTHER PUBLICATIONS

"Conference Record Industry Applications Society IEEE-IAS-1985 Annual Meeting 1985", IEEE Industry Applications Society, Library of Congress No. 80-640527.

Davies, Phil et al., "Three phase control and drive IC for brushless motors", Electronic Engineering, Nov., 1986, p. 51.

Benzer, Robert, "Single-Chip Brushless-Motor Controller", Machine Design, Jun. 9, 1988.

*Primary Examiner*—Bentsu Ro
*Attorney, Agent, or Firm*—Fish & Richardson P.C.

[57] ABSTRACT

A surgical system, adapted to operate with at least one surgical device, has a handpiece containing a motor which is adapted to receive the surgical device. The surgical device is driven through a continuum of positions by the motor output shaft. A controller microprocessor controls the operation of the system. The motor has sensors for generating electrical position signals and the controller is responsive to input signals for defining both a stop position and a reversal position for the surgical device. As a result, the controller initiates operation of the surgical device at the so called stop position and stops operation of the surgical device so that it comes to rest substantially at the stop position. In an oscillatory mode of operation, the controller also forces reversals to occur at a reversal position dictated by the system, under the control of the user, unless a stall condition is sensed, in which case the reversal takes place as soon as possible. In connection with an arthroscopic cutting device, the control enables the surgeon to control, for example, the opening of the aperture through which tissue and fluids are removed from the surgical site during the reversal and start/stop conditions.

8 Claims, 10 Drawing Sheets

MOTOR CONTROLLED SURGICAL SYSTEM AND METHOD HAVING SELF CLEARING MOTOR CONTROL

CROSS REFERENCE TO RELATED APPLICATIONS

The present application is a continuation-in-part of co-pending application 08/420,243, filed Apr. 11, 1995, entitled MOTOR CONTROLLED SURGICAL SYSTEM AND METHOD HAVING POSITIONAL CONTROL, now U.S. Pat. No. 5,602,449, which is a continuation-in-part of application Ser. No. 08/135,297, filed Oct. 12, 1993, abandoned, which is a continuation-in-part of application Ser. No. 07/867,871, filed Apr. 13, 1992, now U.S. Pat. No. 5,270,622, all of which are incorporated by reference herein.

BACKGROUND OF THE INVENTION

This invention generally relates to motor driven surgical systems, and, more particularly, to a system for controlling the relative positions of components of an all digital motor controlled surgical system.

Digital speed control systems for controlling the rotational speed of brushless motors used, for example, with arthroscopic cutting devices are now well known.

These brushless motor controlled devices typically adapt to a surgical assembly and use an all digital well defined system such as that disclosed in U.S. patent application Ser. Nos. 420,243 and 135,297 and U.S. Pat. No. 5,270,622, referred to above. They provide excellent control over the rotational speed and position of the motor armature, which enables precise and accurate control of the surgical assembly through an appropriate gear reduction between motor and assembly. Such digital control systems provide an advancement over the prior analog controlled systems using, typically, brushless motors.

In all of these motors, however, the relative position of the rotatable driven surgical member to the fixed housing in which it rotates, and in particular, the relative opening of, for example, a cutting aperture at the distal tip of the surgical device is unknown. In this respect, both brushless (all digital) and brush motors suffer the same difficulty, in that the nature of the aperture is unknown to the control system and, in particular, there was no way of maintaining any fixed relationship, known to the control system, between the rotatable portion of the removable rotary tip of the surgical device and its enclosing fixed housing. In co-pending U.S. patent application Ser. No. 420,243, however, substantial control over the motor position is achieved. In fact, the motor can be repeatedly stopped with the aperture in a fully open position.

It is therefore an object of the invention to improve the control over and cutting by the rotational portion of the driven surgical member, and in particular, to provide an apparatus which enables the physician to improve the efficiency and effectiveness of an arthroscopic cutting device and the accuracy with which the cutting process proceeds.

It is a general object of this invention to advance the state of the art in the control of brushless motors, particularly in connection with controlled arthroscopic cutting devices.

Another object of this invention is to provide an all digital motor controlled surgical cutting device having improved cutting effectiveness, accuracy, and response repeatability.

Another object of the invention is to provide an improved motor controlled system which has particular application in surgical procedures.

Yet another object of the invention is a method and apparatus which accurately and repeatable control motor driven surgical tools.

SUMMARY OF THE INVENTION

In keeping with these objects, and others which will become apparent hereinafter, the invention employs an all digital surgical control system for a brushless motor. The system comprises a digital signal processor for supplying command signals indicative of a desired motor operation. The processor or controller generates, for each phase of motor drive, and in response to the external control signals, a digital commutation signal to rotate the armature. A digital pulse width modulated signal having a duty cycle established by the control signals controls armature rotational speed.

The system further has a switching element, for example a multi-phase bridge, in digital communication with the controller. The bridge is operative for generating, for each phase, and in response to each commutation signal and each pulse width modulated signal, a digital two-state control signal having an on-state which lasts for the duration of the pulse width modulated signal.

The system still further has elements in digital communication with the controller, for generating, as the motor rotates, position sensor signals indicative of armature position. The controller is operative for processing the position sensor signals to generate a digital signal indicative of the actual armature rotational speed.

The invention features, in one aspect, shutting down or stopping the motor, either at the end of an oscillatory mode wherein the motor is constantly and automatically reversed, or in a continuous mode, at the end of a cutting cycle, so that the driven portion of a surgical device stops at a known and specified location, for example, an aperture open position.

In accordance with the invention, there is provided a mode of operation, in addition to a continuous mode of operation in which the drive motion of the motor oscillates, the motor first being driven in one direction and then in the other direction. In this mode of operation, the system provides for the option of adding an oscillatory or reversal stop position at which reversal of direction takes place. Preferably, in operation, the controller allows rotation of the motor in one direction for a fixed length of time before reversing direction when, after the allowed time expires, the driven surgical member reaches the predetermined or selected oscillatory stop position.

In this manner, the surgical device can be controlled so that it always starts, and/or reverses, at a known position at which an aperture at a distal end of the surgical device has a known open, closed, or partially opened characteristic.

The invention provides, advantageously, repetitive and precise operation of the surgical cutting device which promotes both efficiency and reliability for the system when the controller is used, for example, in arthroscopic surgery for the cutting and removal of tissue and other material.

The surgical control system has particular application for drawing tissue into a motor driven surgical cutting blade for resectioning and/or for fluid control.

The invention thus relates to a surgical system adapted to operate with at least one surgical device, the surgical system having a handpiece containing a motor, the motor having a motor armature, and the motor being adapted to receive and drive the surgical device. The surgical device is driven at least in an oscillatory mode by the handpiece. The system features a controller for controlling the driving of the surgical device, sensors in the motor for generating electrical signals indicative at least of a motor drive relative position, and the motor being responsive to the relative position signals the motor being responsive to the relative position electrical signals for identifying a current position of the motor drive relative to the motor drive relative position, a position identifier for identifying to the controller a start/stop position for the motor surgical device for leaving the device in a known condition. A stop switch can be electrically connected to the controller, and the controller is responsive to actuation of the stop switch for stopping driving movement of the surgical device at substantially an open position.

The invention features a start switch, electrically connected to the controller, and the controller being responsive to the start switch for actuating the driven movement of the surgical device, in an oscillatory mode. The controller further is responsive to a stall condition at start-up of or during the oscillatory mode (where the motor speed is zero and the applied motor voltage is at a set maximum), wherein the controller reverses the direction of the motor as soon as possible after the stall condition is sensed. In a preferred embodiment, the invention features continuously reversing the direction of rotation whenever a stall condition is sensed. In this manner the rate of oscillatory reversal is substantially increased, to help clear the aperture of the device.

The novel features which are considered a characteristic of the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

FIG. 8 is a cross-sectional view through. FIG. 7;

DESCRIPTION OF PARTICULAR EMBODIMENTS

Figure 1:
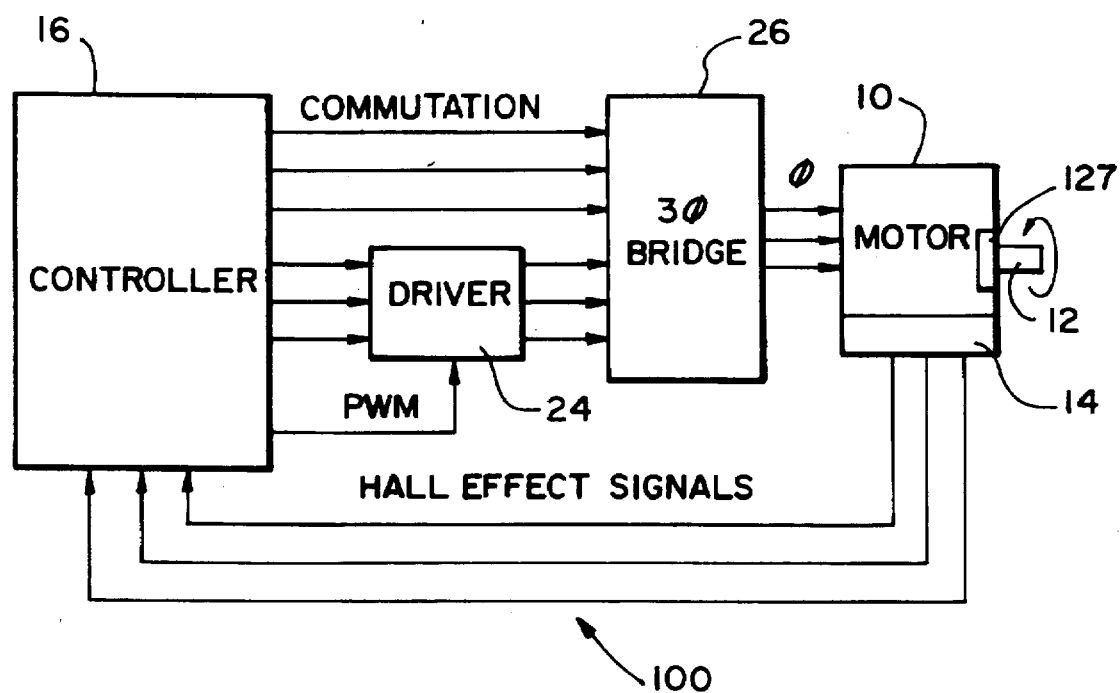
FIG. 1 is a general block diagram of the overall all-digital speed and position control system according to the invention.

The present invention is illustrated in terms of a control system for controlling the speed and more particularly for purposes of this disclosed invention, the relative position, of a motor, here a brushless three-phase, DC motor. Referring now to FIG. 1 the all-digital motor control system of this invention has a brushless, three-phase, DC motor 10 having a rotating armature 12. The motor has a plurality of conventional Hall effect sensors 14 mounted about the armature to sense armature position.

Figure 2:
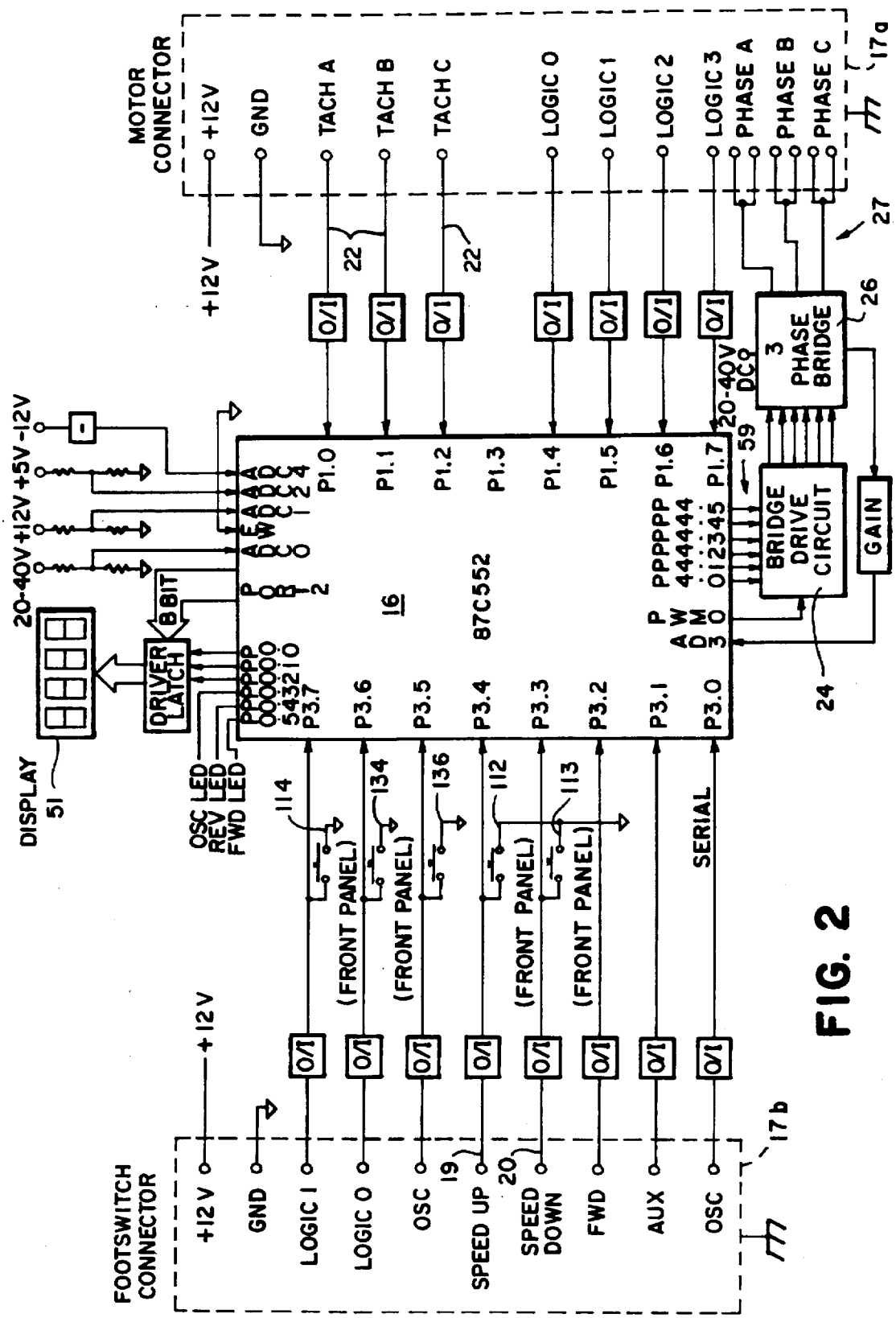
FIG. 2 is a detailed block diagram of a particular embodiment of the system of FIG. 1.

The system includes a digital signal processor or controller 16, preferably constituted as integrated circuit chip manufactured by Philips as No. 87C552. Controller 16 connects to motor 10 and a foot pedal switch (not shown) through connectors 17a and 17b respectively. Controller 16 generates an internal digital speed signal indicative of a desired armature speed based on the speed-up and speed-down signals over lines 19 and 20 (FIG. 2). The processor (or controller) 16, as will be described in detail below, also determines a motor output speed indicative of the actual armature speed from signals over lines 22 from the Hall effect devices.

Upon power turn-on, controller 16 executes a software program. Controller 16 generates a set of six commutation signals, two for each phase of the illustrated four pole brushless motor, together operative for rotating the armature. More specifically, the controller in the illustrated embodiment, includes in its program, a look-up table having a listing of six commutation bit patterns, each pattern representing a discrete command for the armature, as a function of the angular position of the armature, as determined by the signals from the Hall effect devices. The commutation signals are fed through, and processed in, a three-phase bridge circuit 26, and optionally, through a bridge driver circuit 24 (see FIG. 2), whereby three position control signals, one for each phase of the motor drive, are output to the motor 10 over lines 27. (The Hall effect sensors 14 sense rotation of the armature and generate two-state Hall effect signals, in response to which the controller 16 generates the commutation signals.)

Figure 3:
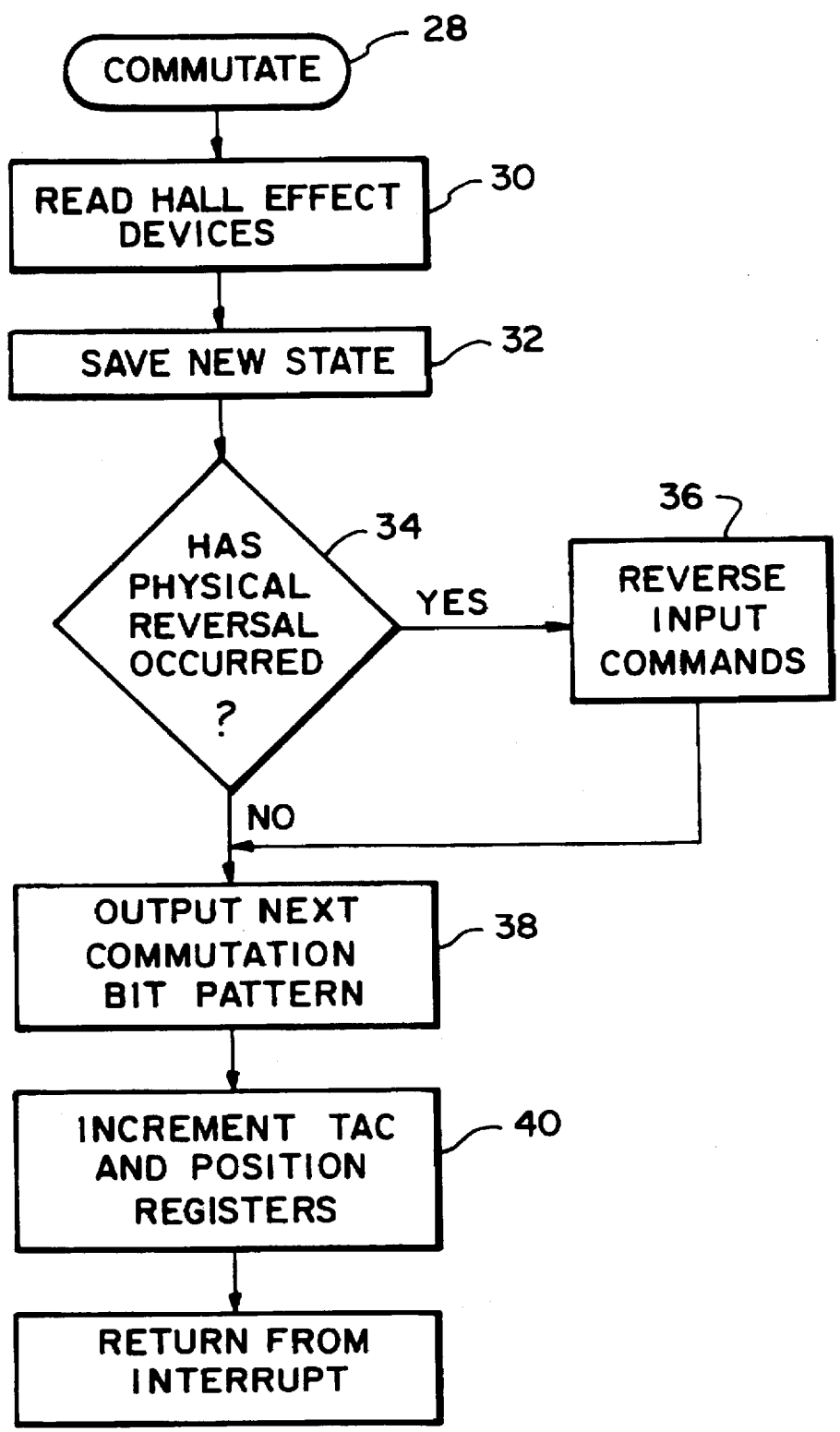
FIG. 3 is flow chart depicting part of the operation of the controller.

This latter aspect of the controller 16 is illustrated in the operations flow chart of FIG. 3. The generation of the commutation signals is indicated by block 28. The reading of the Hall effect sensors is denoted by block 30. The new state is stored at 32. When the controller 16 recognizes that a physical reversal of the armature has occurred (block 34), the reverse input command is given (block 36) and the next commutation bit pattern is output to the motor (block 38). If no reversal has occurred, the commutation bit pattern is sent without passing through block 36. Thereafter, an internal counter, operative for generating a tachometer (TAC) signal, and the position registers, as described hereinafter, are incremented (block 40). The controller then returns from the interrupt. (For the illustrated four pole (3 phase) motor, the bit pattern changes every 30° of armature mechanical rotation.) The tachometer signal is processed to generate the aforementioned speed signal.

Figures 4, 5:
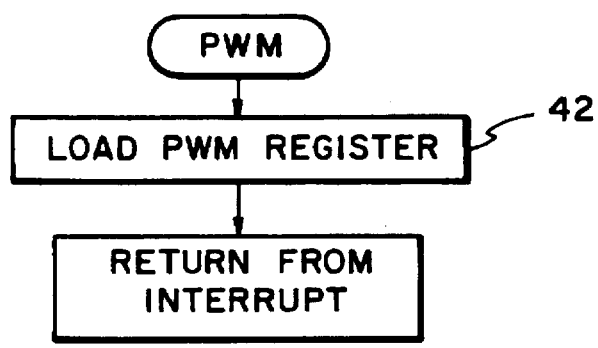
FIG. 4 is a flow chart depicting another aspect of the operation of the controller.
FIG. 5 is a flow chart depicting still another aspect of the controller operation according to the invention.

Referring to FIG. 4, controller 16 also generates, by loading a PWM register in response to the desired speed value, a digital pulse width modulated (PWM) signal having a duty cycle (or pulse width) dependent upon armature rotational velocity. (Block 42) The PWM signal, in the illustrated embodiment, has a fixed PWM cycle of 42.5 microseconds. The PWM signal has a high and a low state. The controller determines the duration of the PWM signal and hence the speed of the armature in the preferred case, from 0–42.5 μs. In this way, the duty cycle of the PWM signal is controlled from 0–100%.

As shown in FIGS. 1 and 2, the PWM signal is fed to a bridge drive circuitry 24 which generates switching signals for the three phase bridge 26 as is well known in the art. In turn, the bridge 26 generates, for each phase, the aforementioned motor control signals. each having an on-state and an off-state.

The Hall effect sensors, as previously mentioned, generate and send relative position signals back to the controller where the signal changes are accumulated as they occur. The resulting counts from a TAC counter are processed by controller 16 to generate a tachometer signal which is delivered by the processor 16 to a display 51 and is indicative of the actual rotational speed of the motor.

Figure 6:
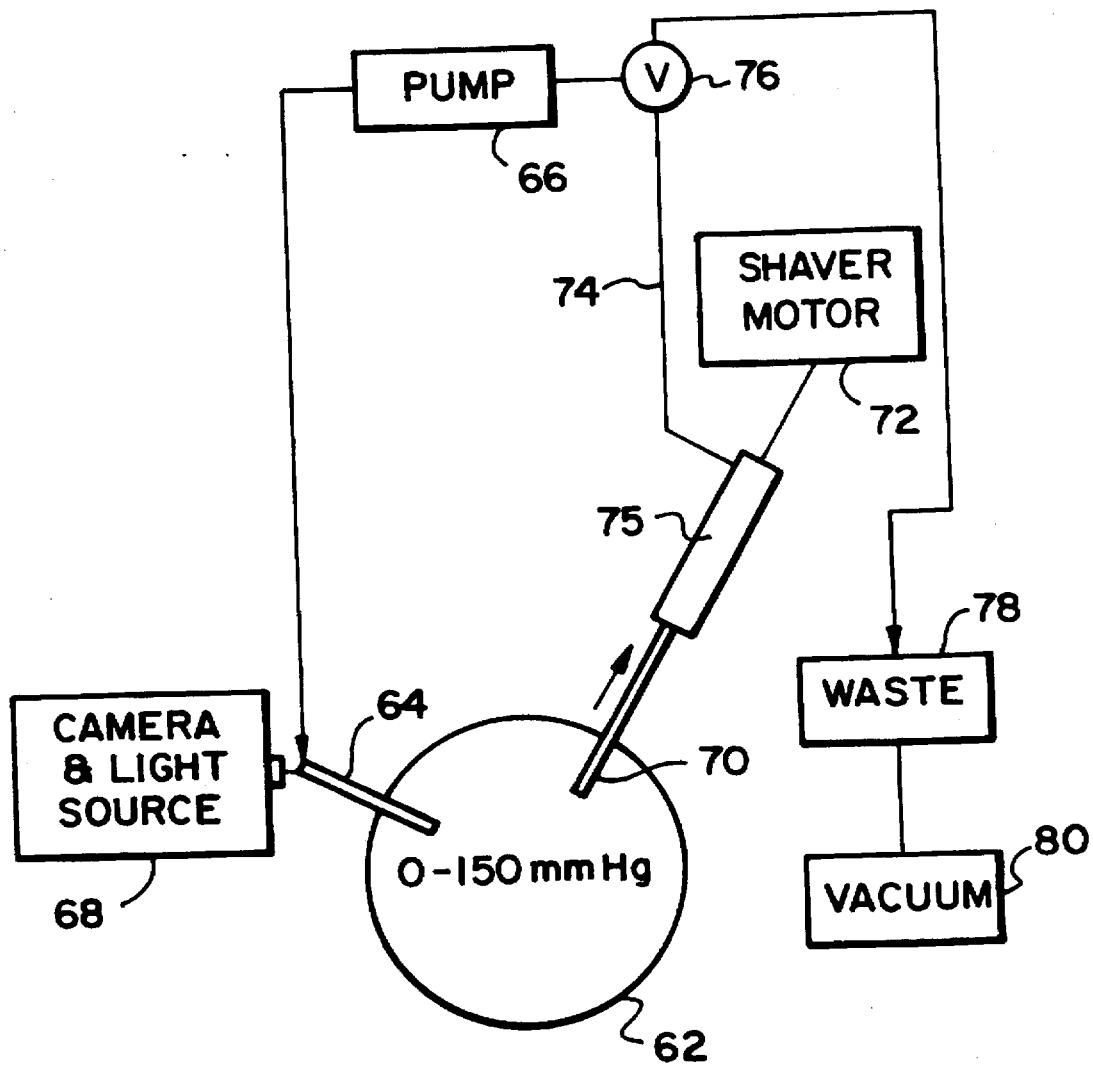
FIG. 6 is a schematic block diagram of a surgical procedure, using the system of the invention.

FIG. 6 is a schematic block diagram showing a setup of a typical modern surgical procedure, for example, an arthroscopy or laparoscopy. A joint or another area of the patient being operated on is shown at 62. A first cannula 64 is introduced into the area and is attached to a source of saline solution. A pump 66 maintains a positive pressure in the joint, for example 0 to 150 mm Hg gage. A video camera and light source 68 are also connected to the cannula 64 for viewing the area and displaying the image on a television monitor (not shown). A second cannula 70 with a surgical instrument at its end is also introduced into the area 62. The instrument, here, is a hand-held shaver with a motor drive 72. The saline, blood and debris from the cutting are removed from the area through a hollow in the cannula 70 and then through a hose 74 which passes to a pinch valve 76, located on the pump housing 66, and which can help regulate flow from the area. The effluent then passes to a waste collector 78 and to a vacuum source 80 which typically maintains a pressure of 150 to 760 mm Hg absolute. Between the cannula 70 and hose 74 is the remainder 75 of a surgical device.

It is important in such procedures that the pressure in the area 62 remain constant. This is particularly difficult to maintain in the area of a joint where the mechanical dimensions of the joint are constantly changing, and the joint is leaking and represents an unstable and unsealed volume. As the surgeon operates the surgical system, opening and closing the connection to the vacuum and removing bits of tissue with the fluid flow, there can be a quickly changing vacuum. It is essential for good surgical procedures that the pressure in the surgical area be constant. Particularly important is that the pressure never become too large, as this would injure the patient. Constant pressure is directly related to accurate control over the velocity of the saline flowing into the area 62. Small changes of pump speed yield very large changes in pressure. It has been found that with the control system of the present invention, a substantially constant pressure, to very tight tolerances, can be maintained. This is particularly achieved with a pulse driven motor in the pump, where the drive pulse duty cycle can be varied, and accordingly where the frequency of revolution can also be varied from a fraction of an RPM to, for example, 1000 RPM. Typical flow rates into a surgical area are from 0.0 to 2.5 liters per minute.

Figure 7:
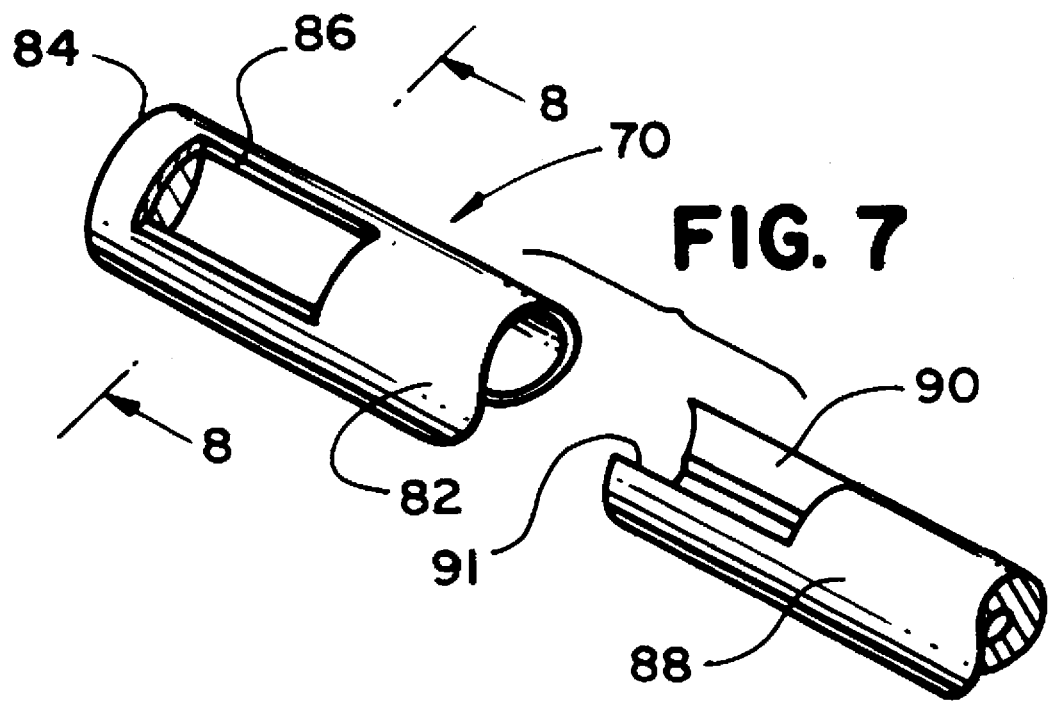
FIG. 7 is a perspective view of a surgical tool.

FIG. 7 is a schematic perspective, partially cut away, exploded view of part of a surgical device, a blade assembly, which would appear at the end of the cannula 70. A fixed hollow tube 82 of the blade assembly, closed at its distal end 84, has an opening which describes typically a cut-out section 86. The rotatable inner blade 88, also a hollow tube, has a cutting surface with sharp edges 91 at its distal end region 90. The inner blade is driven by the motor and rotates inside the tube 82 which is securely housed in the motor assembly. The vacuum draws fluids and debris through the central hollow for removal.

The inner blade is typically driven at a constant speed, and rotates either in a continuous, single direction, mode, or in an oscillatory mode. The inner blade is driven by the motor within the shaver 72 corresponding to motor 10. It is desirable to control accurately the torque applied to the inner blade, because if the torque is too large, for example due to a piece of bone or metal or other fragment getting caught in the spinning tube of the inner blade 88, the inner blade itself or the tube 82, or the cannula 70 may shatter with the result of spraying debris into the patient's joint. The debris, then, must be removed which is not an easy task. Also, there is the resulting attendant trauma to the region. The control system of the present invention provides such a torque control.

As noted above, the system of the present invention applies a voltage or electrical drive energy, for example, a series of pulses with a particular duty cycle, to the brushless motor. The tachometer measures the actual speed of the motor armature, as noted above, and compares the desired armature rotational speed with the actual output speed derived from the Hall effect sensor waveforms (FIG. 10) from the driven motor. If an object becomes stuck inside the surgical device, the motor will normally need more power, and thus will call for an increased duty cycle in the form of more average voltage and/or current. The software compares the actual speed of the motor with the commanded speed of the motor, and if the speed is too slow for the applied voltage, then the controller will decrease the duty cycle, (which correspondingly reduces the average voltage or current), and this will cut down on the torque, and thus will avoid possible fracture of the inner blade 88 or the tube 82. The surgeon may then observe the condition at the end of the cannula through the camera 68; and if something is stuck, increase the flow of saline or manipulate the tool to remove the clogging. It is also desirable in this situation to stop the tool with the aperture open. As will be described below, the invention allows this condition to be attained if originally preset into the system. If need be, also, the surgeon can change the tool.

Figure 8:
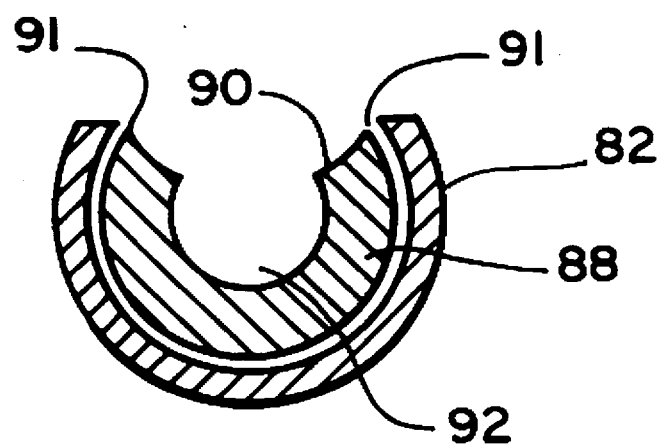

FIG. 8 is a cross-sectional view through the cannula of FIG. 7 but with the inner blade inserted therein. The inner blade 82 with its cutting edge 91, in the present invention, may be driven to rotate one way, and then another, that is, to oscillate. For example, the system can drive the inner blade clockwise for 0.6 seconds, then counter-clockwise for 0.6 seconds, and thereafter repeat that process. As the inner blade body 88 rotates one way and then the other, tissue that moves into the opening 86 is cut, and is then removed by the action of the vacuum, by flushing the saline solution through the interior hollow aperture 92, which feeds ultimately to the hose 74.

It is understood that the oscillatory movement is not limited to rotary inner blades, but may be used for drills, circular rasps, rotary rotating scalpels, and a full range of motor driven tools.

It is also desirable, in accordance with the invention, as noted above, that the inner blade 88 start, and stop, in either mode of operation, a continuous mode of operation or an oscillating mode of operation at a known position. In the continuous mode, the inner blade begins operation in one direction and terminates operation under control of the user, but does not reverse. In this mode, it is desirable that the inner blade start and stop at the same location, for example when its aperture and cutting edges are aligned, that is, substantially, with the aperture in the distal end of tube 82, at cutout section 86. Thus, control upon starting and stopping of the inner blade is desirably achieved, and thereby the aperture may be left open, allowing vacuum and the resulting flow of solution to continually clear the area of the surgical event, or, on the other hand, may be left closed or only partially open when those positions are determined to be desirable. Similarly, the ability to start the operation of the surgical device, at the same location each time, gives the surgeon the ability to predict with substantial certainty the type, location, and quantity of tissue to be resected.

It is also advantageous, and particularly useful for the surgeon, in the oscillatory mode of operation described above, that the reversal of direction always takes place with the aperture in the same condition, that is, preferably open, possibly closed, or at some position therebetween. This provides therefore that, for example, no effluent shall be withdrawn from the joint during the reversal process, or on the other hand that some or a full flow of effluent will be withdrawn from the joint during reversal, at a time when tissue cannot be cut since rotational motion will have stopped, if only momentarily. The ability to predict with certainty that the reversal will take place in a known and predictable manner provides substantial advantage to the described surgical device. In accordance with the invention, the controller is capable of effecting aperture control, as described above, in the following manner.

Figure 9:
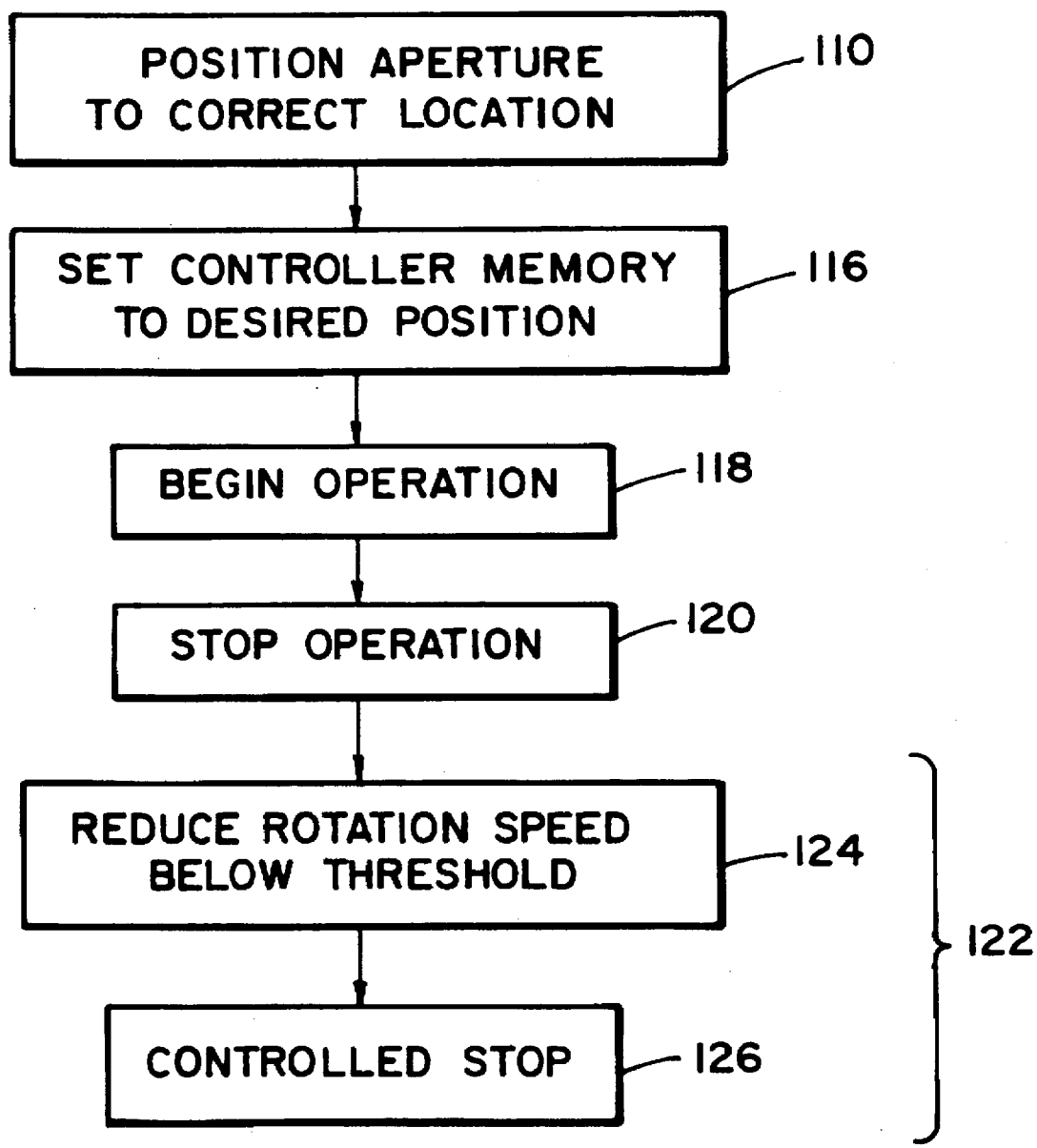
FIG. 9 is a flow chart of another aspect of controller operation according to the invention.

Referring now to both FIG. 2 and the flow chart of FIG. 9, in a preferred embodiment of the invention, the controller 16 operates in an open loop fashion. That is, the controller learns a position from which desired start and stop operations are to be effected, and tracks the position of the driven portion of the surgical device from that location, based upon the Hall effect signals coming from the drive motor over lines 22 and the knowledge, built into the programming of the controller, of the nature of the motor and any gear reduction mechanism interconnected between the motor armature shaft and its eventual output shaft 12. In the illustrated embodiment of the invention, the motor is a four pole (three phase motor) having a 5:1 gear reduction mechanism which thus requires five turns of the armature of motor 10 for each single turn of the output shaft 12.

Upon initial operation, the user, or surgeon, increments the surgical device to position its aperture at its distal end to its correct location (block 110). This can be accomplished effectively by providing a speed up switch 112 which, upon actuation, causes the motor to slowly increment and hence to move the driver inner blade, in one illustrated embodiment, until it properly aligns itself with the opening in tube 82. This can be, as noted above, to provide either an open, closed, or partially open aperture. In the particular embodiment of the invention, switch 112 is complemented by switch 113 so that the motor can increment in either the forward or reverse direction. Once the motor has been set to the desired position, a third switch 114 is actuated to set the controller memory to that position (block 116). This results in clearing a memory counter of controller 16 which is then incremented each time there is a change of state on any of Hall effect switch lines 102, 104, 106.

In the preferred embodiment of the invention, the switches 112 and 113 (or their foot pedal equivalents, if any) are simultaneously depressed. In response, the controller increments the driver inner blade and, upon release of the switches at a desired position, the controller resets the memory counter to "zero", corresponding to the desired start-stop position.

Figure 10:
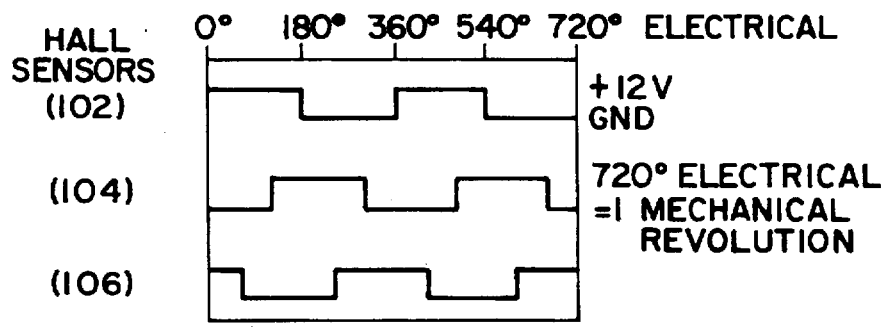
FIG. 10 depicts the Hall effect switch outputs according to the invention.

Referring to FIG. 10, it will be seen from a review of the signals coming from the Hall effect switches that 12 changes of state occur for each 720 degrees of the electrical cycle, corresponding to one complete revolution of the armature. Accordingly, for one complete revolution of the output shaft 12 there are 60 changes of state provided by the motor sensors over lines 22. In the controller, therefore, a counter is provided which counts forward or backward, depending upon the direction of motor rotation, modulo 60, and the controller software recognizes that once set, the motor must stop at a location corresponding to a count of "zero". Thus, after the controller memory is set (to "zero") at 116, continuous or oscillatory operation can be initiated, at 118. During the continuous mode of operation, the motor operates in a first direction (forward or reverse) and continues to do so, in accordance with the description here and above, until a stop command is given.

In the preferred embodiment of the invention, the operation of the motor is initiated by depressing a foot pedal (not shown) and the release of the foot pedal acts as a stop switch to command the controller to terminate rotation of the motor 10. This is indicated at 120. The controller, however after recognizing the actuation of the stop command, continues to rotate the motor so that it will stop at the previously predetermined condition, in this embodiment corresponding to a count of zero in its counter. This is indicated at 122. However, as noted at block 124 if the rotational speed of the motor is greater than a defined threshold, the motor first is slowed down to a speed below that threshold value (for example 1,000 rpm) in accordance with a preferred embodiment of the invention and is then brought to a controlled stop, at the predetermined position, at 126. This occurs, in particular, with brushless motors since, unlike, for example, stepping motors, the motor is built so that the inertia of the motor drive helps to carry the armature forward from position to position.

In the illustrated embodiment of the invention, the control loop operates as an asynchronous, position error, control loop. This method of control is generally simple to implement, however, other methods including synchronous control and/or a velocity error control loop may also be employed, and in certain circumstances may provide improved accuracy in stopping at the start-stop position.

The accuracy with which motor armature position is known is determined by the frequency with which state changes occur over lines 22, and, since 60 state changes occur for each full revolution of the output shaft in this illustrated embodiment (taking into account the 5:1 gear reduction ratio of reducer 127 of the motor), it can be determined that a change of state over lines 22 occurs every 6 degrees of surgical device rotation. (See also FIG. 10) Thus, the accuracy of stopping of the motor is approximately plus or minus 6° (360° of rotation divided by 60) ignoring other errors.

In this open loop control mode, it is also important that the gear reduction ratio have a value "a" that must be an exact multiple of 1/[number of Hall effect state changes per armature revolution] (1/12 in the illustrated embodiment). Otherwise, the position of the driven member may "creep", thus resulting in errors in positioning the surgical device driven member both at the start-stop position, and at the reversal position described below.

In the preferred embodiment of the invention, referring now to FIG. 5, and as noted above, the motor and controller can advantageously operate in an oscillatory mode. In this mode, in a preferred embodiment of the invention, the user has the ability to set a second position, an oscillatory mode reversal position at which the reversal of the motor takes place. Referring to FIG. 5, the operator or surgeon first positions the driven member of the surgical device so that, for example, the driven member is at the correct opening location at which the surgeon desires reversal to take place.

This is indicated at block 130. Once that position is set, (using switch 112 as before), the controller memory is set to record that position. Note that here, the reversal position is set after the start-stop position has been set and accordingly, typically, the position will be at a location other than the start-stop position. A separate tracking counter can be used by the controller for tracking armature position relative to the reversal position. Alternatively the start-stop tracking counter can be used. (The default value for the reversal position is the start-stop position). That value is recorded by the controller and once recorded the surgical device is returned to the precorded start-stop position. This is indicated at block 132. A separate switch 134 can be used to record the oscillatory mode reversal position. However, in accordance with the preferred software of Appendix A, once the controller is in the oscillatory mode of operation, the procedure noted above of simultaneously closing and then releasing switches 112 and 113 can be used to move the driver inner blade to a desired position and storing the position in an oscillatory tracking counter when the switches are released.

Oscillatory mode operation can then be effected by actuating a switch 136. Upon actuating switch 136, the motor begins to move in a first direction and will continue to do so for a fixed length of time, in the illustrated embodiment. In other embodiments, the number of revolutions can be set, however, in the preferred embodiment, it is considered better to use a fixed length of time, for example less than 1 second, and preferably about 0.4 seconds. Once oscillatory operation begins, as noted at block 138, the direction of movement of the surgical device continues in the same direction until time out of the time period has occurred. This is indicated at 140. After the time out occurs, the controller continues the direction of motor rotation until it reaches the oscillatory reversal position at which location the controller effects a reversal of direction. This is indicated at 142. The time out timer is then reset, for example to 0.6 seconds, and the system recycles unless a stop command had been given as indicated at 144. If, during the time when the time out counter is running, a stop command is given as noted at 146, the system escapes from the time out loop to terminate rotation at the next traversal of the start-stop position (unless rotation velocity exceeds threshold as noted above). This is indicated at 148.

Figure 5A:
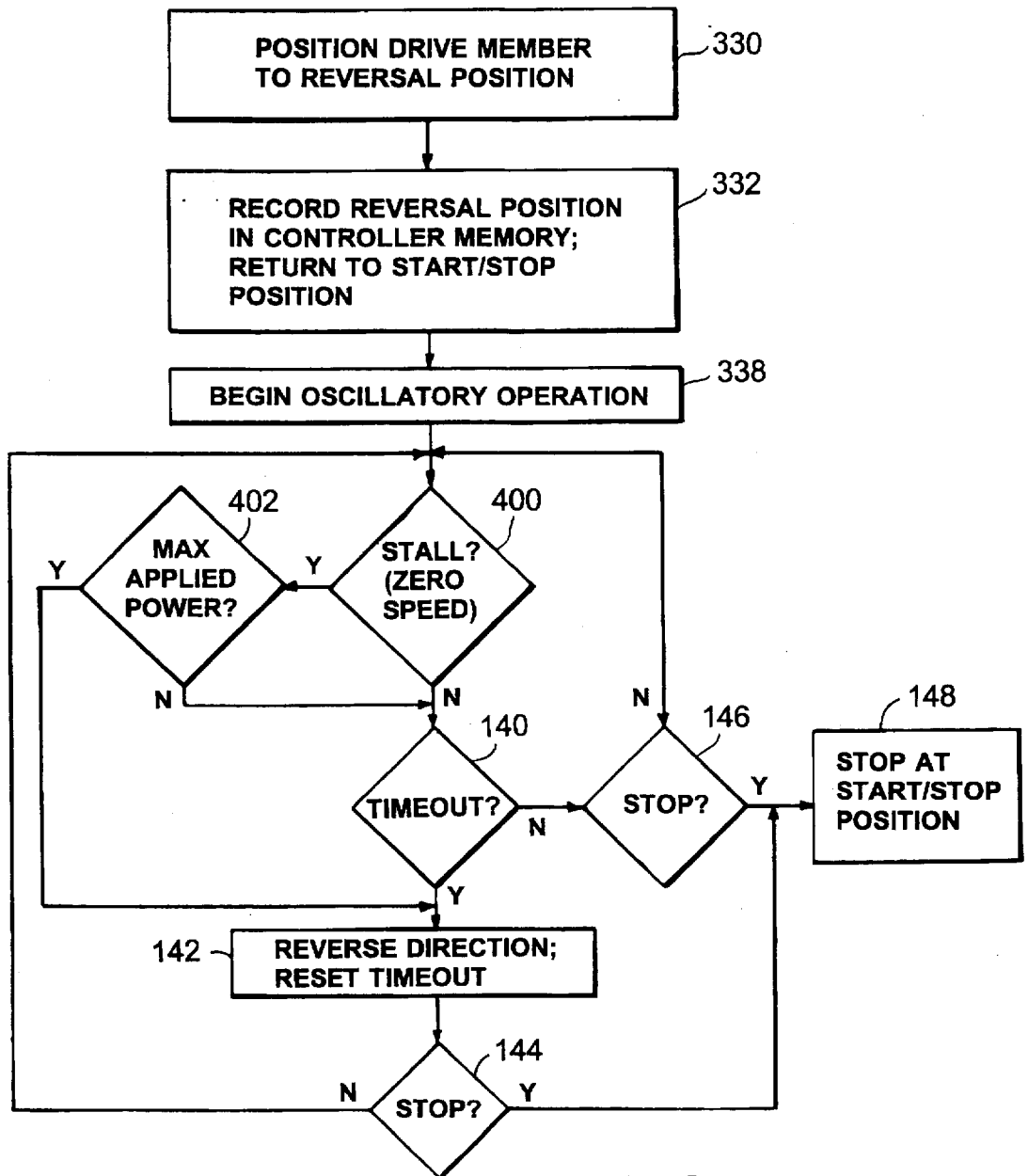
FIG. 5A is a flow chart depicting a particular aspect of the controller operation in the oscillatory mode.

In accordance with a preferred embodiment of the invention, referring to FIG. 5A, the surgical device, when stopped with the aperture partially or fully opened, can be positioned to encompass the tissue or bone to be removed. The fully opened aperture is illustrated in FIGS. 7 and 8. Prior to beginning oscillatory motion, however, the reversal position is set at 330, and is recorded at 332, as noted above. The system is then placed in an oscillatory mode and power is applied to the blade to begin oscillatory operation at 338. In the oscillatory mode, in accordance with the preferred embodiment of the invention, the blade will oscillate approximately 2.5 times per second to remove and clear the material in the aperture.

In certain circumstances, where either the quantity or nature of the material in the aperture causes the motor to stall, the stall condition is sensed at 400, 402, by the controller. The stall condition is defined as zero rotational speed (400) with an applied voltage which is at the limit to which voltage can be applied to the motor (402). Under this circumstance, rather than waiting for the full time out at 140 of, for example, 0.4 seconds, before reversing direction of the motor drive, the motor drive is immediately reversed and full torque is applied in order to clear the aperture and effect proper cutting action. (Note that under this condition of zero speed, there is no reverse EMF with which to contend.)

This results in a faster reversal of the blade by the motor and, under a continuing stall condition, will result in a continuing reversal of motor direction at a rate of, for example, approximately 12.5 times per second in the illustrated embodiment of the invention. Fast and aggressive reversal of the motor direction continues until the aperture is cleared and the system returns to a normal, oscillatory time-out condition, indicated by steps 140, 142, 144, 146, 148 as described in connection with FIG. 5 or until the stop command is given.

At any time during the surgical procedure, if a new surgical device is introduced into the motor, or if the physician desires to reset either the start-stop or oscillatory reversal positions, the procedures noted above in connection with FIGS. 5, 5a and 9 need to be repeated. Thereafter, operation of the system proceeds as described hereinabove.

In accordance with the preferred embodiment of the invention, there has been described an open loop system. It is possible that in the open loop configuration the relative position of oscillatory reversal or start-stop positions may vary due to decoupling of the tracking mechanism with the armature physical position due to extraneous influences. It is therefore possible, should further security be desired, or for other reasons, to operate the system in a closed loop configuration by adding addition magnets and/or sensing elements to the handpiece and/or the surgical device.

Figure 11:
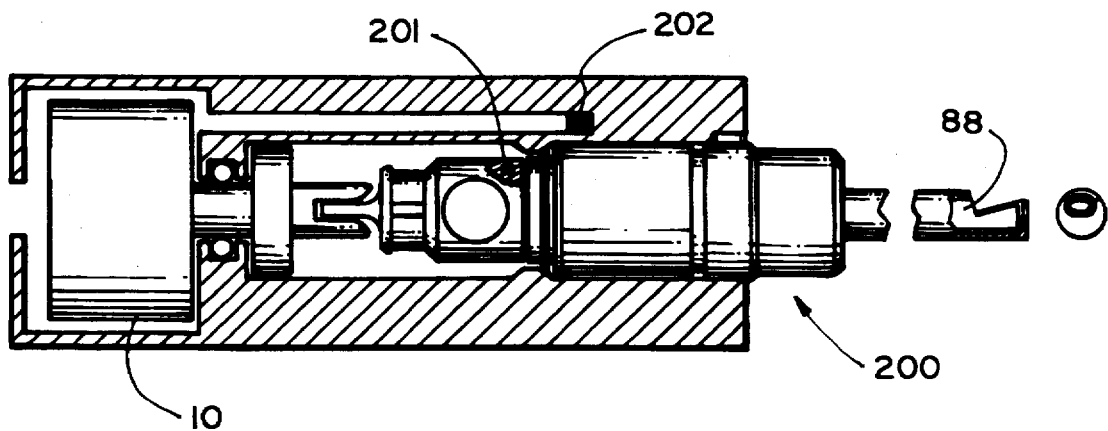
FIG. 11–13 are schematic diagrams of different embodiments of the closed loop method of operation.

Referring now to FIG. 11, there is illustrated a motor 10 connected to a surgical device 200 and wherein a magnet 201 is embedded in the outer circumference of the proximal end of the rotating driven surgical member, here inner blade 88. A Hall effect receiving element 202 is embedded within the motor handpiece to establish an absolute reference point for the surgical system. Thus, the controller, which can receive an electrical signal from the Hall effect receiving switch 202, can determine with precision when the inner blade is positioned opposite the Hall effect receiving switch 202. In this embodiment, in accordance with the preferred use of the closed loop method, the controller uses the signal from Hall effect switch receiving element 202 to supplement and check the signals which are derived as noted above in connection with the open loop process. There are two reasons for this. First, the physician may not want to use, as either the start/stop position or the reversal position, the aperture setting corresponding to the alignment of the magnet 200 in the proximal end of the inner blade with the Hall effect switch receiver 202. (In fact, unless the devices are one-way keyed, this is a random alignment.) Second, because only one magnet is provided in this embodiment, and because it is impossible to stop the brushless motor of the current design "on a dime", the actual end stopping point may not only be variable, but will be other than that designated by the magnet; and in fact, the end point will be a function of the rotational speed of the motor at the time the magnet passes by receiver 202.

The closed loop method can be used to provide the additional control described above in addition to the open loop method.

Figure 12:
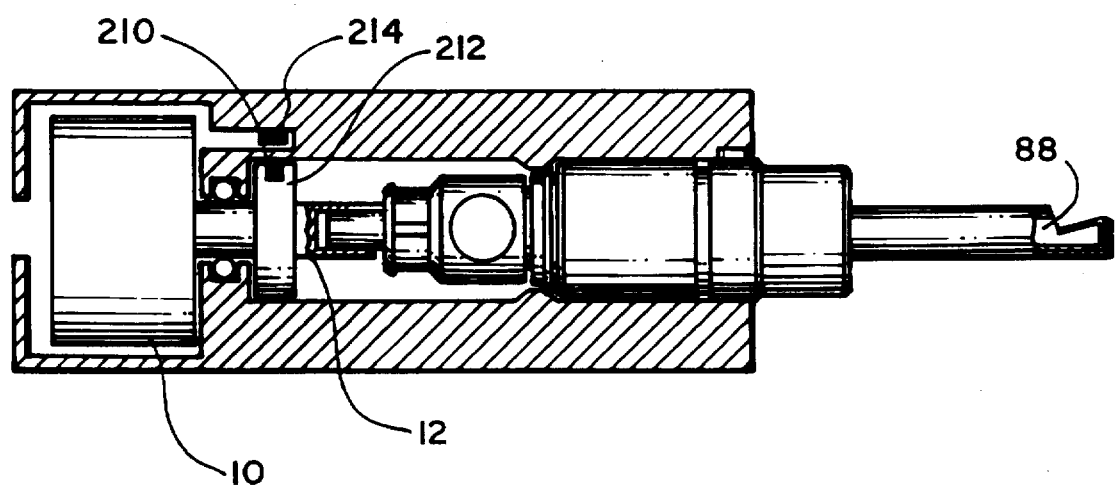

Referring to FIG. 12, in a second embodiment of the closed loop method, a rotating magnet 210 is embedded in moving motor drive shaft 12, at 212. A corresponding Hall effect receiving switch 214 is positioned within the motor handpiece to establish a precise reference point for motor control; however, in this embodiment, the drive shaft into which the surgical device is received must have a single orientation with regard to the driven member in order to properly define the member (aperture) with respect to the drive shaft magnet 210. This embodiment suffers the same resolution issues described above in connection with the embodiment of FIG. 11.

Figure 13:
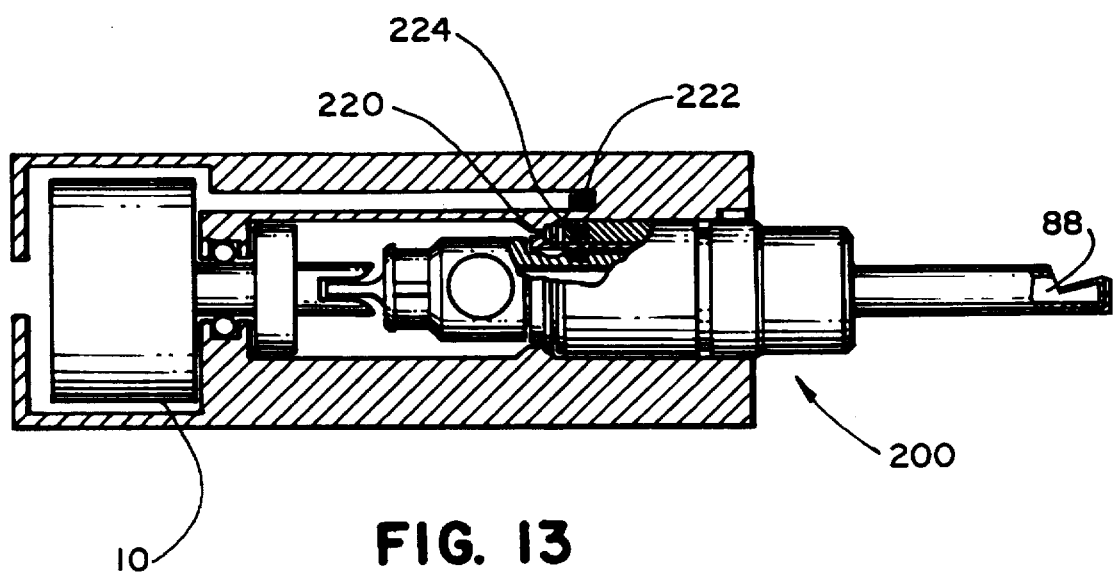

Referring now to FIG. 13, in yet a third embodiment of the closed loop method, a single modulating element, a magnet 220 embedded in the rotating portion of the inner driven member of the surgical device, and aligned with existing receiving Hall effect switches 222 and with already existing device type sensing magnets 224 can provide another method for the controller to determine absolute positioning of the driven rotating member relative to the fixed tube member 82. However, as with the embodiments illustrated in connection with FIGS. 11 and 12, this embodiment also suffers from the same resolution problems which can be resolved by either closed loop or open loop techniques.

Other embodiments of the invention for controlling the stop and start position and the oscillatory reversal position of a driven member of a surgical device relative to the fixed member of the same device will be apparent to those practiced in the art. They might include, for example, designing complex algorithms to monitor and control still conditions, the use of more accurate, higher torque stepper motors as opposed to the brushless motor preferred and described herein, and other methods for increasing the torque of the system. These, and other embodiments of the invention will be apparent to those practiced in these arts that are within the scope of the following claims.

While the invention has been illustrated and described as embodied in an all-digital speed control system for a brushless three-phase DC motor, it is not intended to be limited to the details shown, since various modifications and structural changes may be made without departing in any way from the spirit of the present invention.

What is claimed is:

1. A surgical system adapted to operate with at least one surgical device, the surgical system having a handpiece containing a motor having a motor armature, and the handpiece being adapted to receive and drive said surgical device, said surgical device being driven through a continual of positions by said handpiece, said system comprising a controller for controlling the driving of said surgical device, a start switch electrically connected to the controller, and an oscillatory mode switch electrically connected to said controller, said controller being responsive to actuation of said start switch for starting driven movement of said surgical device in an oscillatory mode when called for by said oscillatory mode switch, and said controller, in response to a powered stall condition, reversing the direction of driven movement of said surgical device.

2. The surgical system of claim 1 further comprising said controller reversing the direction of driven movement each time said controller senses a stall condition.

3. The surgical system of claim 2 further wherein said controller senses a stall condition when it senses zero velocity of the motor armature and a maximum voltage applied to the motor.

4. The surgical system of claim 2 wherein the motor oscillates at approximately twelve cycles per second in a stall oscillating mode.

5. A method for operating a surgical system wherein the surgical system has a handpiece containing a motor which is adapted to receive a surgical device, the surgical device having a fixed member and a driven member, the fixed and the driven members cooperatively arranged to effect severing of tissue when the movable member is driven by said motor in said handpiece, and the handpiece receiving, at a distal end, a proximal end of the surgical device, the surgical device at its distal end defining a variable aperture, which, depending upon the position of the driven member relative to the fixed member can be fully open, fully closed, or partially open, and the surgical system having a control mechanism for controlling operation of the motor, the method comprising the steps of defining for a controller a stop position at which said driven member has a particular relationship to the fixed member;

operating said motor in an oscillatory mode, and reversing the direction of rotation of said motor each time the controller senses a stall condition.

6. The method of claim 5 further comprising the step of defining an oscillatory reversal position of said surgical device at which said oscillatory mode reverses direction, and reversing the direction of the motor in said oscillatory mode only substantially at said oscillatory mode reversal position unless said stall condition occurs, and stopping said motor when said system is in said oscillatory mode in response to a stop command at said stop position.

7. The method of claim 6 further comprising the step of driving said motor in one direction in said oscillatory mode for a fixed period of time unless said stall condition occurs.

8. The method of claim 7 wherein said fixed period of time is less than one second.

* * * * *